US00PP33396P2

(12) United States Plant Patent
Shafer

(10) Patent No.: US PP33,396 P2
(45) Date of Patent: Aug. 24, 2021

(54) **NEW GUINEA *IMPATIENS* PLANT NAMED 'BALCLOAPL'**

(50) Latin Name: *Impatiens hawkeri*
Varietal Denomination: Balcloapl

(71) Applicant: Ball Horticultural Company, West Chicago, IL (US)

(72) Inventor: Gail Shafer, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/190,131

(22) Filed: Mar. 2, 2021

(51) Int. Cl.
*A01H 5/02* (2018.01)
*A01H 6/16* (2018.01)

(52) U.S. Cl.
USPC ..... Plt./318.1

(58) Field of Classification Search
USPC ..... Plt./263.1, 318.1
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of New Guinea *Impatiens* plant named 'Balcloapl', characterized by its white-colored flowers tinted with purplish-red, dark reddish-green colored foliage, and moderately vigorous, mounded growth habit, is disclosed.

1 Drawing Sheet

Latin name of genus and species of plant claimed: *Impatiens hawkeri.*
Variety denomination: 'Balcloapl'.

BACKGROUND OF THE INVENTION

The present invention relates to a new and distinct cultivar of *Impatiens* plant botanically known as *Impatiens hawkeri* and hereinafter referred to by the cultivar name 'Balcloapl'.

The new cultivar originated in a controlled breeding program in Arroyo Grande, Calif. during February 2017. The objective of the breeding program was the development of *Impatiens* cultivars that have large flowers, uniform flower timing, and a moderately vigorous, mounded growth habit.

The new *Impatiens* cultivar is the result of cross-pollination. The female (seed) parent of the new cultivar is the proprietary *Impatiens hawkeri* breeding selection coded GS1458-1, not patented, characterized by its light pink-colored flowers, dark bronze-colored foliage, and moderately vigorous, mounded growth habit. The male (pollen) parent of the new cultivar is the proprietary *Impatiens hawkeri* breeding selection coded GS1865-2, not patented, characterized by its light pink-colored flowers, dark bronze-colored foliage, and moderately vigorous, mounded growth habit. The new cultivar was selected as a single flowering plant within the progeny of the above stated cross-pollination during August 2017 in a controlled environment in Arroyo Grande, Calif.

Asexual reproduction of the new cultivar by terminal stem cuttings since August 2017 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcloapl' as a new and distinct cultivar of *Impatiens* plant:

1. White-colored flowers tinted with purplish-red;
2. Dark reddish-green colored foliage; and
3. Moderately vigorous, mounded growth habit.

Plants of the new cultivar differ from plants of the female parent primarily in having larger diameter flowers. Plants of the new cultivar differ from plants of the male parent primarily in having more branches per plant.

Of the many commercially available *Impatiens* cultivars, the most similar in comparison to the new cultivar is Clockwork Orange Stripe 'Balceboripi', not patented. However, in side by side comparisons, plants of the new cultivar differ from plants of 'Balceboripi' in at least the following characteristics:

1. Plants of the new cultivar have flowers are tinted with a purplish-red color that is different from the light orange-colored tinted flowers of plants of 'Balceboripi'; and
2. Plants of the new cultivar have lighter colored foliage than plants of 'Balceboripi'.

In addition, the new cultivar can be compared to Clockwork Appleblossom 'DANCEL877', U.S. Plant Pat. No. 21,622. However, in side by side comparisons, plants of the new cultivar differ from plants of 'DANCEL877' in at least the following characteristics:

1. Plants of the new cultivar have smaller diameter corollas than plants of 'DANCEL877';
2. Plants of the new cultivar are shorter and narrower than plants of 'DANCEL877'; and
3. Plants of the new cultivar have flowers that are tinted with a purplish-red color that is different from the purplish-pink tinted flowers of plants of 'DANCEL877'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcloapl'. The approximately 15-week-old plants were grown in 4-inch pots for approximately 13 weeks in a greenhouse in West Chicago, Ill. Plants were given one pinch two-weeks prior to transplant.

DETAILED BOTANICAL DESCRIPTION

Figure 1:
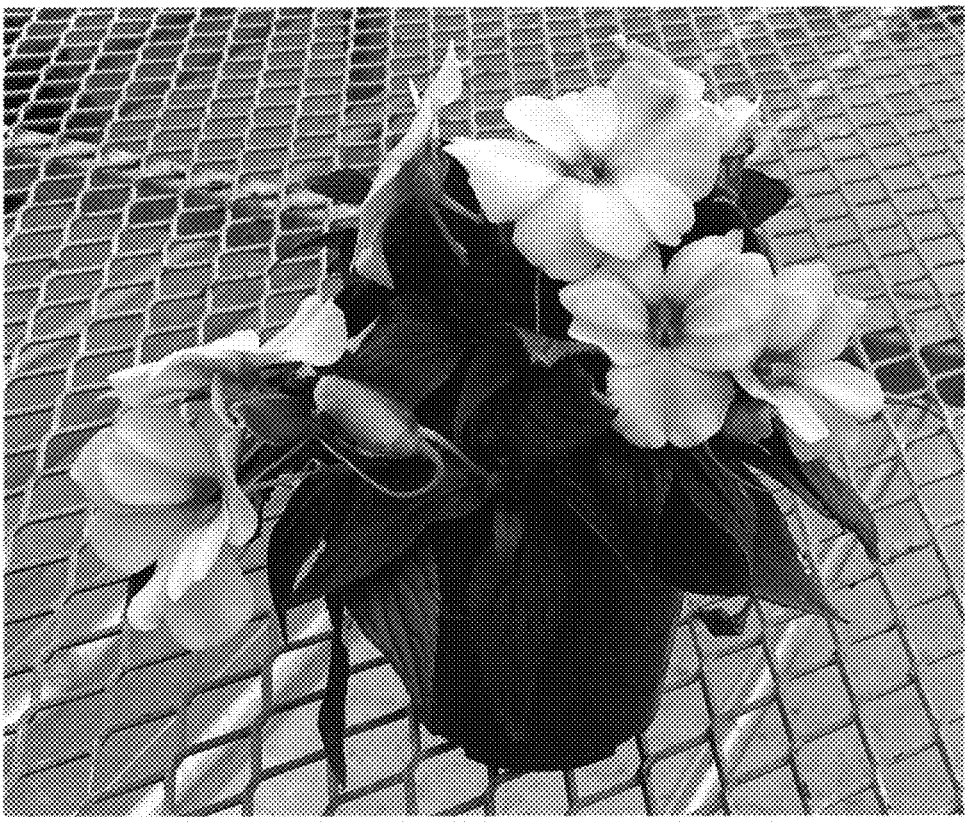
FIG. 1 illustrates a side view of the overall growth and flowering habit of 'Balcloapl'.
Figure 2:
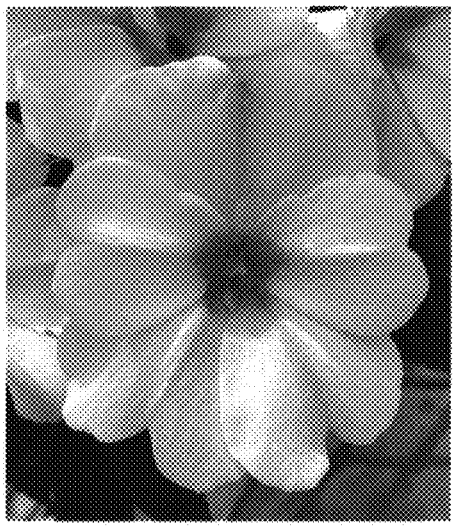
FIG. 2 illustrates a close-up view of an individual flower of 'Balcloapl'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2021 under natural light conditions in Naperville, Ill.

The following descriptions and measurements describe approximately 15-week-old plants produced from cuttings from stock plants and grown in a glass-covered greenhouse under conditions comparable to those used in commercial practice. The plants were grown in West Chicago, Ill. in 4-inch pots for approximately 13 weeks utilizing a soilless growth medium. Plants were given one pinch two-weeks prior to transplant. Greenhouse temperatures were maintained at approximately 70° F. to 75° F. (21° C. to 24° C.) during the day and approximately 68° F. to 74° F. (20° C. to 23° C.) during the night. Supplemental lighting was used. Measurements and numerical values represent averages of typical plants.

Botanical classification: *Impatiens hawkeri* 'Balcloapl'.

Parentage:

*Female parent*.—Proprietary *Impatiens hawkeri* breeding selection coded GS1458-1, not patented.

*Male parent*.—Proprietary *Impatiens hawkeri* breeding selection coded GS1865-2, not patented.

Propagation:

*Type cutting*.—Terminal stem.

*Time to initiate roots*.—Approximately 7 to 8 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, mounded growth habit.

*Size*.—Height from soil level to top of plant plane: Approximately 12.0 cm. Width: Approximately 19.0 cm.

*Branching habit*.—Freely branching. Pinching improves basal branching. Quantity of main branches per plant: Approximately 5.

*Branch*.—Strength: Moderately strong. Length: Approximately 6.5 cm. Diameter at central internode: Approximately 7.0 mm. Length of central internode: Approximately 2.2 cm. Texture: Glabrous. Color of young and mature stems: Closest to 146D with a heavy overlay of 187B.

Foliage description:

*General description*.—Quantity of leaves per main branch: Approximately 10. Fragrance: None. Form: Simple. Arrangement: Whorled with up to 5 leaves per node, opposite if only two leaves at one node.

*Leaves*.—Aspect: Petiole is at an acute angle to stem and leaves are perpendicular to an obtuse angle to stem. Shape: Elliptic. Margin: Serrulate, ciliate. Apex: Acuminate. Base: Attenuate. Venation pattern: Pinnate. Length of mature leaf at center of stem: Approximately 8.0 cm. Width of mature leaf at center of stem: Approximately 3.5 cm. Texture of upper surface: Sparsely pubescent. Texture of lower surface: Glabrous. Color of upper surface of young foliage: 147A to 147B with venation of 187C. Color of lower surface of young and mature foliage: Closest to 147C with a heavy overlay and venation of 187C. Color of upper surface of mature foliage: 147A to 147B tinted with 187A, venation of 187C.

*Petiole*.—Length: Approximately 1.0 cm. Diameter: Approximately 3.0 mm. Texture: Glabrous. Color: 147D with a heavy overlay of 187C.

Flowering description:

*Flowering habit*.—'Balcloapl' is freely flowering under outdoor growing conditions with substantially continuous blooming from spring through autumn and year-round in greenhouse environment.

*Lastingness of individual flower on the plant*.—Approximately 7 to 9 days.

Flower description:

*General description*.—Type: Single. Quantity per plant: Approximately 7. Fragrance: None.

*Bud*.—Rate of opening: Generally takes 1 to 2 days for bud to progress from first color to fully open flower. Quantity showing color per plant: Approximately 3.

*Bud just before opening*.—Shape: Ovoid. Length: Approximately 1.9 cm. Diameter: Approximately 1.2 cm. Color: N57B.

*Corolla*.—Shape: Round, cupped when first open with petals flattening with age. Diameter: Approximately 6.5 cm. Depth: Approximately 1.2 cm. Borne: Above the foliage.

*Petals*.—Quantity: 5. Shape: Obovate. Aspect: Flat. Appearance: Dull. Margin: Entire. Apex: Emarginate. Base of upper petal: Truncate. Base of lateral and lower petals: Attenuate. Length of upper petal: Approximately 3.0 cm. Width of upper petal: Approximately 4.3 cm. Length of lateral petals: Approximately 3.0 cm. Width of lateral petals: Approximately 2.4 cm. Length of lower petals: Approximately 3.5 cm. Width of lower petals: Approximately 3.8 cm. Texture of upper and lower surfaces: Glabrous. Color of upper surface when first and fully open: NN155D lightly tinted in the petal centers with N57D; lateral petals base of N57A; lower petals base of 61A. Color of lower surface when first and fully open: NN155D heavily tinted in the petal centers with N57B.

*Spur*.—Quantity: 1 per flower. Length: Approximately 4.0 cm. Diameter at proximal end: Approximately 2.0 mm. Diameter at distal end: Approximately 1.0 mm. Texture: Glabrous. Color: 145C tinted with N57D at proximal end.

*Peduncle*.—Strength: Moderately strong. Aspect: Acute angle to stem. Length: Approximately 3.0 cm. Diameter: Approximately 2.0 mm. Texture: Glabrous. Color: 145C.

*Sepals*.—Quantity per flower: 4 with one fused to base of upper petal. Sepal arrangement: 1 spurred lower sepal located between 2 side (lateral) sepals. Shape of lateral sepals: Ovate. Shape of lower sepal: Ovate. Apex of all sepals: Acuminate. Length of lateral sepals: Approximately 1.2 cm. Width of lateral sepals: Approximately 6.0 mm. Length of lower sepal: Approximately 1.7 cm. Width of lower sepal: Approximately 1.3 mm. Texture of upper and lower surfaces of all sepals: Glabrous. Color of upper and lower surfaces of lateral sepals: 146B with a heavy overlay of 187C and tips of N186A. Color of upper and lower surfaces of lower sepal: Closest to 62C to 62D with tip of 146B.

*Reproductive organs*.—Androecium: Stamen quantity: 5 per flower, fused around pistil at apex. Anther shape: Hooded. Anther length: Approximately 6.0 mm. Anther color: 155B. Filament color: NN155D tinted with N57B. Pollen amount: Abundant. Pollen color: 155D. Gynoecium: Pistil quantity: 1 per flower. Pistil length: Approximately 5.0 mm. Stigma shape: 5-pointed star. Stigma color: Colorless, transparent. Style color: 146B with a heavy overlay of 187A. Ovary texture: Glabrous. Ovary color: 146B spotted with 187A.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named New Guinea 'Balcloapl', substantially as herein illustrated and described.

* * * * *